United States Patent
Schlitter et al.

(10) Patent No.: US 8,933,277 B2
(45) Date of Patent: Jan. 13, 2015

(54) PROCESS FOR PREPARING POLYMETHYLOLS

(75) Inventors: Stephan Schlitter, Shanghai (CN); Michael Steiniger, Neustadt (DE); Stefan Rittinger, Mannheim (DE); Tilman Sirch, Schifferstadt (DE); Steffen Maas, Bubenheim (DE)

(73) Assignee: BASF SE, Ludwigshafen (DE)

( * ) Notice: Subject to any disclaimer, the term of this patent is extended or adjusted under 35 U.S.C. 154(b) by 687 days.

(21) Appl. No.: 13/144,124

(22) PCT Filed: Jan. 7, 2010

(86) PCT No.: PCT/EP2010/050087
§ 371 (c)(1),
(2), (4) Date: Jul. 12, 2011

(87) PCT Pub. No.: WO2010/079187
PCT Pub. Date: Jul. 15, 2010

(65) Prior Publication Data
US 2011/0272270 A1    Nov. 10, 2011

(30) Foreign Application Priority Data
Jan. 12, 2009  (EP) .................................... 09150373

(51) Int. Cl.
| | | |
|---|---|---|
| *C07C 27/28* | (2006.01) | |
| *C07C 29/80* | (2006.01) | |
| *C07C 31/24* | (2006.01) | |
| *B01D 3/34* | (2006.01) | |
| *C07C 29/141* | (2006.01) | |
| *C07C 45/75* | (2006.01) | |
| *C07C 45/82* | (2006.01) | |

(52) U.S. Cl.
CPC .............. *C07C 29/80* (2013.01); *C07C 29/141* (2013.01); *C07C 45/75* (2013.01); *C07C 45/82* (2013.01)
USPC .................. 568/854; 203/14; 203/18; 203/74; 203/77; 203/80; 568/463; 568/853; 568/862

(58) Field of Classification Search
USPC .............. 203/14, 18, 29, 74, 77, 80; 568/463, 568/853, 854, 862
See application file for complete search history.

(56) References Cited

U.S. PATENT DOCUMENTS

| | | | |
|---|---|---|---|
| 2,271,134 A | 1/1942 | Will et al, | |
| 3,808,280 A | 4/1974 | Merger et al. | |
| 3,818,680 A | 6/1974 | Marquis | |
| 4,230,533 A | 10/1980 | Giroux | |
| 4,258,440 A | 3/1981 | McGowan | |
| 4,288,640 A | 9/1981 | Schuster et al. | |
| 4,386,018 A | 5/1983 | Merger et al. | |
| 4,386,219 A | 5/1983 | Merger et al. | |
| 4,407,703 A * | 10/1983 | Featherstone | 203/43 |
| 4,543,163 A * | 9/1985 | Stamerjohn et al. | 203/37 |
| 4,745,228 A | 5/1988 | Decker et al. | |
| 5,068,361 A | 11/1991 | Richter et al. | |
| 5,074,967 A * | 12/1991 | Fowlkes | 203/14 |
| 5,235,118 A * | 8/1993 | Morris et al. | 568/862 |
| 5,564,123 A | 10/1996 | Grassick | |
| 5,981,769 A | 11/1999 | Baur et al. | |
| 6,018,074 A * | 1/2000 | Kratz et al. | 560/234 |
| 6,048,441 A | 4/2000 | Auer et al. | |
| 6,115,840 A | 9/2000 | Hastings | |
| 6,187,971 B1 | 2/2001 | Kratz et al. | |
| 6,201,160 B1 | 3/2001 | Brudermüller et al. | |
| 6,240,563 B1 | 6/2001 | Niedermeyer | |
| 6,426,438 B1 | 7/2002 | Fischer et al. | |
| 6,448,457 B1 | 9/2002 | Hesse et al. | |
| 6,809,224 B2 * | 10/2004 | Dernbach et al. | 568/493 |
| 7,767,865 B2 | 8/2010 | Sirch et al. | |
| 2004/0040829 A1 | 3/2004 | Gall et al. | |
| 2004/0267055 A1* | 12/2004 | Sirch et al. | 568/595 |
| 2005/0153834 A1 | 7/2005 | Weiguny et al. | |
| 2005/0222435 A1 | 10/2005 | Weiguny et al. | |
| 2005/0222436 A1 | 10/2005 | Weiguny et al. | |
| 2008/0004475 A1 | 1/2008 | Sirch et al. | |
| 2010/0113805 A1 | 5/2010 | Windecker et al. | |
| 2010/0113836 A1 | 5/2010 | Sirch et al. | |
| 2010/0168445 A1 | 7/2010 | Pinkos et al. | |
| 2010/0240913 A1 | 9/2010 | Pinkos et al. | |
| 2010/0256398 A1 | 10/2010 | Pinkos et al. | |

(Continued)

FOREIGN PATENT DOCUMENTS

| | | |
|---|---|---|
| CA | 1222717 A1 | 6/1987 |
| CA | 1242309 A1 | 9/1988 |
| DE | 1618143 A1 | 10/1970 |
| DE | 1941633 A1 | 3/1971 |
| DE | 1957591 A1 | 5/1971 |
| DE | 2040501 A1 | 2/1972 |
| DE | 2261044 A1 | 6/1973 |
| DE | 3823213 A1 | 1/1990 |

(Continued)

*Primary Examiner* — Virginia Manoharan
(74) *Attorney, Agent, or Firm* — Drinker Biddle & Reath LLP

(57) ABSTRACT

A process is provided for recovering components from a low boiler mixture which is obtained in the distillation of hydrogenation effluents from the preparation of polymethylols, by multistage distillation of the low boiler mixture having a tertiary amine, water, methanol, a polymethylol, a methylolalkanal, an alcohol and an alkanal with a methylene group in the alpha position to the carbonyl group. A first distillation stage involves separating the low boiler mixture into a higher-boiling, predominantly water-rich fraction and into a lower-boiling aqueous organic fraction having the tertiary amine. A second distillation stage involves separating the aqueous organic fraction from the first distillation stage into a predominantly amine-containing fraction and a further amine-depleted fraction. The tertiary amine is trimethylamine or triethylamine and the bottom temperature in the second distillation stage is at least 110° C.

15 Claims, No Drawings

(56) References Cited

U.S. PATENT DOCUMENTS

| | | | |
|---|---|---|---|
| 2011/0015429 A1 | 1/2011 | Pinkos et al. | |
| 2011/0130318 A1 | 6/2011 | Maas et al. | |

FOREIGN PATENT DOCUMENTS

| | | |
|---|---|---|
| DE | 19750532 A1 | 5/1999 |
| DE | 10100552 A1 | 7/2002 |
| DE | 10308489 A1 | 9/2004 |
| DE | 10317545 A1 | 11/2004 |
| EP | 44444 A1 | 1/1982 |
| EP | 122367 A2 | 10/1984 |
| EP | 126288 A2 | 11/1984 |
| EP | 133510 A1 | 2/1985 |
| EP | 0251111 A2 | 1/1988 |
| EP | 0522368 A1 | 1/1993 |
| EP | 0612714 A1 | 8/1994 |
| EP | 640367 A1 | 3/1995 |
| EP | 0895982 A1 | 2/1999 |
| EP | 0928782 A2 | 7/1999 |
| EP | 1030827 A1 | 8/2000 |
| EP | 1568678 A1 | 8/2005 |
| GB | 1140184 A | 1/1969 |
| GB | 1213345 A | 11/1970 |
| GB | 1362071 A | 7/1974 |
| WO | WO-95/32171 | 11/1995 |
| WO | WO-96/29323 A1 | 9/1996 |
| WO | WO-97/31883 A1 | 9/1997 |
| WO | WO-98/17614 A1 | 4/1998 |
| WO | WO-98/28253 A1 | 7/1998 |
| WO | WO-99/44974 A1 | 9/1999 |
| WO | WO-03/078057 A1 | 9/2003 |
| WO | WO-03/078058 A1 | 9/2003 |
| WO | WO-03/078059 A1 | 9/2003 |
| WO | WO-03/078310 A2 | 9/2003 |
| WO | WO-2008/000650 A1 | 1/2008 |
| WO | WO-2008/107333 A1 | 9/2008 |
| WO | WO-2008/116810 A1 | 10/2008 |
| WO | WO-2008/152001 A1 | 12/2008 |
| WO | WO-2009/059913 A1 | 5/2009 |
| WO | WO-2009/080504 A1 | 7/2009 |
| WO | WO-2009/100989 A2 | 8/2009 |
| WO | WO-2010/003934 A1 | 1/2010 |
| WO | WO-2010/031719 A1 | 3/2010 |
| WO | WO-2010/066673 A2 | 6/2010 |
| WO | WO-2010/066674 A2 | 6/2010 |

* cited by examiner

PROCESS FOR PREPARING POLYMETHYLOLS

CROSS-REFERENENCE TO RELATED APPLICATIONS

This application is a national stage application (under 35 U.S.C. §371) of PCT/EP2010/050087, filed Jan. 7, 2010, which claims benefit of EP09150373.0, filed Jan. 12, 2009.

BACKGROUND OF THE INVENTION

The invention relates to a process for recovering components from a low boiler mixture which is obtained in the distillation of hydrogenation discharges from the preparation of polymethylols.

Polymethylols, for example neopentyl glycol ("NPG") and trimethylolpropane ("TMP"), are used in the plastics sector for production of paint systems, coatings, polyurethanes and polyesters.

On the industrial scale, polymethylols are usually prepared by the Cannizzaro process. In order to prepare trimethylolpropane by this process, n-butyraldehyde is reacted with an excess of formaldehyde in the presence of an inorganic base. This likewise forms one equivalent of an inorganic formate as a coproduct. The separation of the salt of trimethylolpropane is complicated and requires additional work. Moreover, the inorganic salt—if it can be utilized in a profitable manner—must be worked up and purified. The occurrence of the coproduct otherwise constitutes a loss of the stoichiometrically used amounts of sodium hydroxide solution and formaldehyde. In addition, the yields in this inorganic Cannizzaro reaction are unsatisfactory in relation to n-butyraldehyde, since high-boiling constituents are formed in the course of the reaction, which cannot be utilized further.

Similar problems to those outlined for trimethylolpropane exist in the preparation of other polymethylols such as trimethylolethane (from n-propanal and formaldehyde) or trimethylolbutane (from n-pentanal and formaldehyde) or neopentyl glycol (from isobutyraldehyde and formaldehyde).

To avoid these disadvantages, WO 98/28253 disclosed a multistage process for preparing polymethylols, in which aldehydes having 2 to 24 carbon atoms are first condensed in a first stage (aldol reaction) with formaldehyde using tertiary amines as a catalyst to give the corresponding methylolalkanals, and then hydrogenated in a further stage (hydrogenation) to give the corresponding polymethylols. This multistage process is typically referred to as the hydrogenation process. This process is low in coproducts.

After the first stage of the hydrogenation process, unconverted aldehydes and a portion of the amine base are generally removed by distillation from the methylolalkanals formed and recycled.

In the distillation bottoms there remain—as well as the methylolalkanals formed—water, the adducts of formic acid and the tertiary amines used (amine formate) and formic acid itself.

In general, the polymethylolalkanal is obtained by these processes as a 20 to 70% by weight aqueous solution.

The polymethylolalkanal-containing solution is hydrogenated in a second stage in order to convert the polymethylolalkanals to the corresponding polymethylols, such as TMP or NPG.

The reaction discharge from the hydrogenation is typically an aqueous polymethylol mixture which comprises polymethylol, tertiary amine, water and organic secondary components, for example an adduct of tertiary amine and formic acid (amine formate). The aqueous polymethylol mixture is therefore typically purified by distillatively removing low boilers from the polymethylol compound.

In the distillative removal of the low boilers, the top product obtained in the condenser is a mixture of low boilers. For example, the low boiler mixture may comprise tertiary amine, unconverted aldehyde and water. More particularly, the low boiler mixture comprises alcohols which have formed by hydrogenation of the alkanals used in the process, such as isobutanol from isobutyraldehyde, or n-butanol from n-butyraldehyde, and methanol from formaldehyde.

The recycling of such a low boiler mixture into the first stage of the hydrogenation process (aldol reaction) is not advantageous, since the low boiler mixture comprises methanol and the corresponding alcohol from the unconverted aldehyde (isobutanol in the NPG process), which exert an adverse effect in the aldol reaction.

Relatively high methanol contents lead, for example, to by-products such as neopentyl glycol methyl ether and/or methyl acetals, through reaction of unconverted aldehydes, such as isobutyraldehyde and formaldehyde or methylolalkanes, with methanol.

Further by-products are, for example, 3,3-dimethoxy-2,2-dimethylpropanol, which is obtained in the trimethylolpropane or neopentyl glycol preparation.

The formation of the by-products mentioned leads to a reduction in the yield in relation to the aldehyde used as the reactant.

In the aldol reaction, methanol leads not just to a reduction in the yield as a result of side reactions, but it can additionally be removed from the remaining components only with very great difficulty, since methanol and the aldehydes used have a similar boiling point. When, however, the intention is to recycle the unconverted starting aldehydes into the aldol reaction, this means that a significant amount of the aldehydes must also be removed together with methanol, in order that aldehyde can be recycled into the process with a minimum of methanol content. Otherwise, there would be accumulation of methanol in the aldol reaction, which would result in the above-described increased formation of by-products.

Similarly, the presence of isobutanol in the aldol reaction leads to a worsened yield, since it is steam-volatile and can be removed by distillation from the aldehyde used as the reactant only with difficulty.

Utilization of the low boiler mixture by distillative separation is not trivial, since the boiling points of the substances present in the low boiler mixture are close to one another and some of these substances form azeotropes.

A disadvantage is especially the presence of isobutanol in the NPG preparation, since isobutanol forms, with water, a low-boiling heteroazeotrope with a miscibility gap.

In addition, the low boiler mixture contains dissolved carbon dioxide, which forms in the hydrogenation stage as a result of hydrogenation of formaldehyde, and formic acid, which is not present in free form but rather as salts with the amine in the aqueous solution. The presence of salts further complicates the distillation.

In the context of the invention, it has now been found that, even by means of a multistage distillation of the low boiler mixture from stage d), a separation into utilizable components is complicated by the fact that the unconverted aldehydes present in the low boiler mixture reduce the volatility of the tertiary amines used, especially of TMA, such that a removal of the tertiary amines from the other organic constituents succeeds only insufficiently or is associated with high yield losses.

BRIEF SUMMARY OF THE INVENTION

It was an object of the present invention to develop a process for purifying a low boiler mixture obtained in the preparation of polymethylols, which enables the substances of value present in this mixture to be utilized. More particularly, the tertiary amine used as the basic catalyst should be recovered, in order to be able to recycle it into the aldol reaction. In this case, the tertiary amine recycled should be very substantially free of methanol, so that there is no increase or accumulation of the methanol concentration in the aldol reaction, which would result in the increased formation of by-products.

More particularly, a virtually complete removal of the tertiary amines used should also be achieved, while the yield losses should be minimized.

It was a further aim to keep the apparatus complexity for the distillation as low as possible, in order to be able to provide an economically viable workup process.

The object of the present invention is achieved by a process for recovering components from a low boiler mixture which is obtained in the distillation of hydrogenation discharges from the preparation of polymethylols, by multistage distillation of the low boiler discharge comprising a tertiary amine, water, methanol, polymethylol of the formula (I)

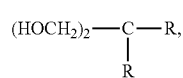

methylolalkanal of the formula (II)

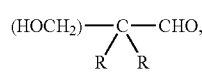

alcohol of the formula (III)

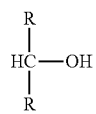

and an alkanal with a methylene group in the α position to the carbonyl group,
and in which each R is independently a further methylol group or an alkyl group having 1 to 22 carbon atoms or an aryl or aralkyl group having 6 to 22 carbon atoms,
a first distillation stage involving a separation the low boiler mixture into a higher-boiling, predominantly water-rich fraction and into a lower-boiling aqueous organic fraction comprising the tertiary amine,
and the second distillation stage involving separating the aqueous organic fraction from the first distillation stage into a predominantly amine-containing fraction and a further amine-depleted fraction,
wherein the tertiary amine is trimethylamine or triethylamine, and the bottom temperature in the second distillation stage is 110° C. and more.

A DETAILED DESCRIPTION OF THE INVENTION

The low boiler mixture used in the process according to the invention is preferably obtained in a multistage reaction involving, in stage a), condensing alkanals in an aldol reaction with formaldehyde in the presence of tertiary amines as a catalyst to give methylolalkanals of the formula (II), and then, in stage b), distillatively separating the reaction mixture obtained from stage a) into bottoms comprising predominantly compounds of the formula (II), and a top stream comprising low boilers, and, in stage c), hydrogenating the bottom discharge from stage b) and then, in a stage d), distilling the discharge from stage c), the low boiler mixture being removed from stage d).

In the first process stage a) (aldol reaction), alkanals are generally reacted in an aldol reaction with formaldehyde in the presence of tertiary amines as a catalyst.

Formaldehyde is generally used in the process as an aqueous formaldehyde solution. Industrially available formaldehyde is typically sold in aqueous solution in concentrations of 30, 37 and 49% by weight. However, it is also possible to use formaldehyde solutions of up to 60% by weight in the process.

Industrial formaldehyde generally comprises formic acid as a result of the preparation. The degradation products of formic acid can reduce the service life of the hydrogenation catalyst in the downstream hydrogenation stage, which can result in a decrease in the yield of polymethylols. In a particular embodiment, formaldehyde which has a formic acid content of 150 ppm or less is used. Such formaldehyde can, as described in application PCT/EP2008/052240, be obtained by treating formaldehyde or an aqueous formaldehyde solution with basic ion exchangers.

In the aldol reaction (stage a)), it is possible to use alkanals with a methylene group in the α position to the carbonyl group.

For instance, it is possible with preference to use aliphatic alkanals having 2 to 24 carbon atoms as starting materials, which may be straight-chain or branched or else comprise alicyclic groups.

It is equally possible to use araliphatic alkanals as starting materials, provided that they comprise a methylene group in the α position to the carbonyl group. In general, aralkylalkanals having 8 to 24 carbon atoms and preferably having 8 to 12 carbon atoms are used as starting materials, for example phenylacetaldehyde. Particular preference is given to aliphatic alkanals having 2 to 12 carbon atoms, for example 3-ethyl-, 3-n-propyl-, 3-isopropyl-, 3-n-butyl-, 3-isobutyl-, 3-sec-butyl-, 3-tert-butyl-butanal and corresponding -n-pentanals, -n-hexanals, -n-heptanals; 4-ethyl-, 4-n-propyl-, 4-isopropyl-, 4-n-butyl-, 4-isobutyl-, 4-sec-butyl-, 4-tert-butylpentanals, -n-hexanals, -n-heptanals; 5-ethyl-, 5-n-propyl-, 5-isopropyl-, 5-n-butyl-, 5-isobutyl-, 5-sec-butyl-, 5-tert-butyl-n-hexanals, -n-heptanals; 3-methylhexanal, 3-methylheptanal; 4-methylpentanal, 4-methylheptanal, 5-methylhexanal, 5-methylheptanal; 3,3,5-tri-methyl-n-pentyl-, 3,3-diethylpentyl-, 4,4-diethylpentyl-, 3,3-dimethyl-n-butyl-, 3,3-di-methyl-n-pentyl-, 5,5-dimethylheptyl-, 3,3-dimethylheptyl-, 3,3,4-trimethylpentyl, 3,4-dimethylheptyl-, 3,5-dimethylheptyl-, 4,4-dimethylheptyl-, 3,3-diethylhexyl-, 4,4-dimethylhexyl-, 4,5-dimethylhexyl-, 3,4-dimethylhexyl-, 3,5-dimethylhexyl-, 3,3-di-methylhexyl-, 3,4-diethylhexyl-, 3-methyl-4-ethylpentyl, 3-methyl-4-ethylhexyl-, 3,3,4-trimethylpentyl-, 3,4,4-trimethylpentyl-, 3,3,4-trimethylhexyl-, 3,4,4-trimethyl-hexyl-, 3,3,4,4-tetramethylpentylaldehyde; especially $C_2$- to $C_{12}$-n-alkanals.

In addition to the particularly preferred use of isobutyraldehyde, which is used to prepare neopentyl glycol, it is also possible with preference to use, as starting materials, n-butyraldehyde to prepare trimethylolpropane, acetaldehyde to prepare pentaerythritol, propionaldehyde to prepare trimethylolethane, and n-pentanal to prepare trimethylolbutane.

Isobutyraldehyde is generally used in the process in pure form (GC area %>99%). Commercially available isobutyraldehyde is typically supplied in purities of 99.5% (without water) with an n-butyraldehyde content of less than 0.1%, the water content generally being up to 2.5%.

A high isobutyraldehyde content is generally advantageous, since n-butyraldehyde leads to increased TMP formation, which has to be removed from NPG. In addition, further by-products can be formed, such as isobutanol or isobutyric acid, which usually have to be removed as low-boiling alcohols after the hydrogenation.

However, it is also possible to use isobutyraldehyde with a content of less than 99.5%, for example with a content of 95 to 98%.

The tertiary amines used are trimethylamine ("TMA") or triethylamine ("TEA"). Particular preference is given to using trimethylamine ("TMA") as the tertiary amine in the reaction.

The aldol reaction can be performed with or without addition of organic solvents or solubilizers. The addition of solvents or solubilizers may be found to be advantageous especially in the case of use of long-chain alkanals as starting materials. The use of solvents which form suitable low-boiling azeotropic mixtures with the low-boiling compounds in the individual distillations of the process according to the invention may allow the energy expenditure in these distillations to be lowered and/or the distillative removal of the low boilers from the high-boiling compounds to be facilitated.

Examples of suitable solvents include cyclic and acyclic ethers such as THF, dioxane, methyl tert-butyl ether, or alcohols such as methanol, ethanol or 2-ethylhexanol.

In the aldol reaction, the molar ratio of alkanal added fresh in each case to the amount of formaldehyde added is appropriately between 1:1 and 1:5, preferably 1:1 to 1:3.

The amount of tertiary amine catalyst added in the aldol reaction in relation to the alkanal added is generally 0.001 to 0.2 and preferably 0.01 to 0.07 equivalent, i.e. the amine is typically used in catalytic amounts.

The aldol reaction is generally performed at a temperature of 5 to 100° C. and preferably of 15 to 80° C., and the residence time is generally set to 0.25 to 12 hours depending on the temperature.

The reaction regimes described for the aldol reaction can be performed at a pressure of generally 1 to 30 bar, preferably 1 to 15 bar, more preferably 1 to 5 bar, and appropriately under the autogenous pressure of the reaction system in question.

The aldol reaction can be performed batchwise or continuously. The aldol reaction can be performed in a stirred tank reactor or in a reaction tube. The aldol reaction is preferably performed in a continuous stirred tank reactor or a continuous stirred tank cascade. To establish the residence time, a portion of the reaction discharge from one stirred tank can be recycled into the particular stirred tank reactor.

The discharge from the aldol reaction comprises typically unconverted starting compounds, such as formaldehyde, alkanals and the tertiary amine catalyst used, with or without water.

The discharge from the aldol reaction further comprises a methylolalkanal of the formula (II)

in which each R is independently a further methylol group or an alkyl group having 1 to 22 carbon atoms or an aryl or aralkyl group having 6 to 22 carbon atoms. Examples of methylolalkanals are hydroxypivalaldehyde, which is formed in the case of use of isobutyraldehyde as a reactant, or dimethylolbutanol, which is formed in the case of use of n-butyraldehyde as a reactant.

Typically, the discharge also comprises impurities and by-products from the aldol reaction, such as formic acid, which can form by Cannizzaro or Tishchenko reaction from formaldehyde, and formate salts of the amine catalysts used, such as trimethylammonium formate.

The discharge from the aldol reaction is subsequently typically worked up by distillation (stage b)).

In this case, the discharge from the aldol reaction is sent to a distillation apparatus, typically a column, in which it is separated into volatile and nonvolatile constituents. The distillation conditions are generally selected such that one fraction forms from low boilers, in which the essential components present are unconverted alkanal, with or without water, formaldehyde and methanol. This so-called low boiler fraction can be recycled into the first stage of the hydrogenation process, the aldol reaction, or be sent to a further workup stage.

After the removal of the low boiler fraction, what remains in the distillative workup outlined is a nonvolatile bottom product which consists essentially of methylolalkanal (II), for example hydroxypivalaldehyde, water, formic acid and amine formate.

In the case of use of TMA as the tertiary amine, the distillation conditions are selected such that TMA is also present partly in the low boiler fraction and is present to a minor degree in the bottom product. In the case of use of TEA, the distillation conditions are selected such that TEA is enriched in the bottom product.

The distillative removal should preferably be effected at moderate pressure in order not to decompose the methylolalkanals (II) by elevated temperature. For example, hydroxypivalaldehyde can be converted to hydroxypivalic acid neopentyl glycol ester (HPN). On the other hand, the pressure should not be too low, in order still to condense the low-boiling alkanals, such as isobutyraldehyde, and any amine base, for example trimethylamine, at the top.

The distillation should also not take place at too low a pressure because the solubility of alkanal (II), such as hydroxypivalaldehyde (HPA), in the aqueous solution declines to about 3% by weight generally below about 60° C., depending on the alkanal and methanol content.

In addition, the discharge from the aldol reaction should be separated such that the amount of methanol in the low boiler stream is kept as low as possible, in order that the methanol concentration does not accumulate in the aldol reaction. Methanol is generally introduced via the aqueous formaldehyde solution, which, according to the preparation conditions, comprises about 0.5 to 3% by weight of methanol.

The boiling point of methanol is generally lower than that of the unconverted alkanal, such that methanol is enriched at the top of the column, thus resulting in an accumulation of the methanol concentration in the process.

In order to keep the methanol concentration low, various measures can be taken.

One advantageous measure is to use low-methanol formaldehyde as a reactant in the aldol reaction.

It is further possible to discharge methanol from the process together with unconverted alkanal, which leads to a loss of alkanal.

In a preferred embodiment, the distillation is, however, performed under specific conditions, such that methanol is retained sufficiently in the column bottoms. This preferred embodiment of the distillative separation of the discharge from the aldol reaction is described in application PCT/EP2008/052240.

In this embodiment, the distillative separation into a low boiler fraction and the bottom product is performed generally at 50 to 200° C., preferably at 90 to 160° C., and at a pressure of generally 0.1 mbar to 10 bar, preferably of 0.5 to 5 bar, especially at atmospheric pressure, in a distillation column. The distillation column is typically operated at a top pressure in the range from 0.5 to 1.5 bar.

In the top region, a two-stage condensation is preferably provided, in which the vapors are first conducted into a partial condenser operated at a temperature in the range from 50 to 80° C., the condensate of which is at least partly recycled into the distillation column, and in which the vapors uncondensed in the partial condenser are fed to a downstream condenser operated at a temperature in the range from −40 to +30° C., the condensate of which is at least partly discharged.

The condensate of the partial condenser is preferably recycled into the distillation column to an extent of more than 70% by weight and more preferably fully. The condensate is preferably recycled into the top of the column. The condensate of the downstream condenser is preferably discharged to an extent of at least 70% by weight.

The partial condenser is operated at a temperature in the range from 50 to 80° C. and preferably 55 to 60° C. The downstream condenser is operated at a temperature in the range from −40 to +30° C. and preferably −10 to +10° C. The top pressure is more preferably 1 to 1.2 bar.

The bottom of the distillation column is preferably connected to an evaporator with a short residence time, which is operated at a temperature in the range from 90 to 130° C., more preferably from 100 to 105° C. The evaporator is more preferably a falling film evaporator; it is also possible with preference to use a wiped film evaporator or a short path evaporator. What is essential is that a short residence time and hence a low thermal stress are achieved. The evaporator can be supplied with heat in a suitable manner, for example with 4 bar steam.

The distillation column preferably has internals for increasing the separating performance. The reaction discharge of the aldolization is preferably fed in within a spatial region between ¼ and ¾ of the theoretical plates of the distillation column, more preferably in a spatial region between ⅓ and ⅔ of the theoretical plates of the distillation column. For example, the feed may be somewhat above the middle of the theoretical plates (ratio 3:4).

The distillative internals may, for example, be present as a structured packing, for example as a sheet metal packing such as Mellapak 250 Y or Montz Pak, B1-250 type. It is also possible for a structured packing with relatively low or increased specific surface area to be present, or a fabric packing or a structured packing with another geometry such as Mellapak 252 Y can be used. What are advantageous in the case of use of these distillative internals are the low pressure drop and the low specific liquid holdup compared to, for example, valve trays.

The condensate obtained in the partial condenser is predominantly water, which is preferably fed to the column completely as reflux. In the case of preparation of NPG, for example, the condensate obtained may be a mixture which comprises about 10% by weight of isobutyraldehyde, about 5% by weight of amine base such as trimethylamine, about 1% by weight of hydroxypivalaldehyde and about 5% by weight of methanol as well as water, when isobutyraldehyde is used as the reactant. In these cases, the residual vapors comprise the predominant amount of isobutyraldehyde and amine base such as trimethylamine. These are precipitated very substantially in the downstream condenser. The cooling medium used here may preferably be very cold water (e.g. about 5° C.) or a coolant mixture (e.g. glycol-water at, for example, −20° C.).

Preference is given to discharging a mixture enriched with methylolalkanal (II), for example hydroxypivalaldehyde or dimethylolbutanal, from the bottom of the evaporator. Discharge from the circulation system is also possible.

The relatively nonvolatile bottom product from the distillative separation of the discharge from the aldol reaction can, to reduce the thermal stress, be cooled before further workup in a cooler with a cooler temperature in the range from 50 to 80° C., more preferably 55 to 60° C.

The bottom discharge thus obtained from stage b) can subsequently be hydrogenated in stage c).

The bottom discharge from stage b) of the hydrogenation process comprises methylolalkanal of the general formula (II) and is hydrogenated in stage c) of the hydrogenation process to the corresponding polymethylols ("hydrogenation").

In the hydrogenation, preference is given to using catalysts which comprise at least one metal of transition groups 8 to 12 of the Periodic Table of the Elements, such as Fe, Ru, Os, Co, Rh, Ir, Ni, Pd, Pt, Cu, Ag, An, Zn, Cd, Hg, preferably Fe, Co, Ni, Cu, Ru, Pd, Pt, more preferably Cu, preferably on a support material.

The support material used is preferably a support material composed of the oxides of titanium, of zirconium, of hafnium, of silicon and/or of aluminum.

The usable catalysts can be prepared by processes known from the prior art for preparing such supported catalysts. Preference may also be given to using supported catalysts which comprise copper on an aluminum oxide- or titanium oxide-containing support material in the presence or absence of one or more of the elements magnesium, barium, zinc or chromium. Such catalysts and preparation thereof are known from WO 99/44974.

In addition, supported copper catalysts as described, for example, in WO 95/32171 and the catalysts disclosed in EP-A 44 444 and DE 19 57 591 are suitable for the hydrogenation.

The hydrogenation can be performed batchwise or continuously, for example in a reactor tube filled with a catalyst bed, in which the reaction solution is passed over the catalyst bed, for example in trickle or liquid phase mode, as described in DE-A 19 41 633 or DE-A 20 40 501. It may be advantageous to recycle a substream of the reaction discharge, if appropriate with cooling, and to pass it through the fixed catalyst bed again. It may equally be advantageous to perform the hydrogenation in a plurality of reactors connected in series, for example in 2 to 4 reactors, in which case the hydrogenation reaction in the individual reactors upstream of the last reactor is performed only up to a partial conversion of, for example, 50 to 98%, and only in the last reactor is the hydrogenation completed. It may be appropriate to cool the hydrogenation discharge from the preceding reactor before its entry into the next reactor, for example by means of cooling apparatus or by injecting cold gases, such as hydrogen or nitrogen, or introducing a substream of cold reaction solution.

The hydrogenation temperature is generally between 50 and 180° C., preferably 90 and 140° C. The hydrogenation pressure employed is generally 10 to 250 bar, preferably 20 to 120 bar.

The hydrogenation feed is generally mixed with tertiary amine upstream of the hydrogenation reactor inlet until the hydrogenation discharge has a pH of 7 to 9. It is also possible to feed the hydrogenation feed and the tertiary amine separately into the reactor and to mix them there. The tertiary amines used may be the aforementioned tertiary amines, especially TMA.

The reaction discharge from the hydrogenation (stage c)) is typically an aqueous polymethylol mixture which comprises a polymethylol of the formula (I)

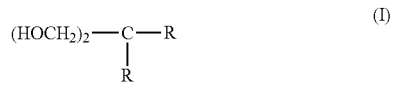

in which each R is independently a further methylol group or an alkyl group having 1 to 22 carbon atoms or an aryl or aralkyl group having 6 to 22 carbon atoms, a tertiary amine, water and the adduct of tertiary amine and formic acid (amine formate).

The aqueous polymethylol mixture preferably has the following composition:
20 to 90% by weight of polymethylol (I),
0 to 10% by weight of methanol,
0 to 5% by weight of tertiary amine,
0 to 5% by weight of organic secondary compounds,
0.01 to 5% by weight of the adduct of tertiary amine and formic acid (amine formate),
remainder water.

The aqueous polymethylol mixture more preferably has the following composition:
50 to 80% by weight of polymethylol (I),
0.1 to 5% by weight of methanol,
0.01 to 5% by weight of tertiary amine,
0 to 5% by weight of organic secondary compounds,
0.01 to 5% by weight of the adduct of tertiary amine and formic acid (amine formate),
remainder water.

The organic secondary compound present may, for example, be the hydrogenated form of the alkanal used, specifically an alcohol of the formula (III)

in which each R is independently as defined above.

The aqueous polymethylol mixture is preferably purified by removing low boilers from the polymethylol compound.

The low boilers are more preferably removed from the aqueous polymethylol mixture by distillation (stage d)).

The distillation is preferably performed in such a way that low boilers, such as water, alcohol of the formula (III), methanol and tertiary amine, are removed under reduced pressure via the top.

Typically, a portion of the amine formates reacts during the distillation in the column bottom or in the stripping section of the column with polymethylol compounds to form the free amines and the formates of the polymethylol compounds. This preferably forms the monoester of formic acid and of the polymethylol compound, which is referred to in the context of this disclosure as polymethylol formate.

The amines released by the transesterification reaction are generally removed in the distillation together with the other low boilers at the top of the column.

The distillation should therefore be regulated such that the concentration of the polymethylol formates formed in the bottom discharge is kept low and the target product, the polymethylol, is of maximum purity. This is preferably done by selecting, in the distillation, a bottom temperature above the evaporation temperature of the polymethylol formate, such that the polymethylol formates are completely or very substantially completely converted to the gas phase by evaporation.

The improvement in the yield and in the product quality brought about by this measure is probably attributable to the fact that the polymethyol formates typically have higher boiling points than the other low boilers, and the polymethylol formates are therefore generally precipitated in the rectifying section of the columns at an appropriate reflux ratio. The polymethylol formates precipitated in the rectifying section can hydrolyze with water to reform formic acid and the polymethylol compound. The formic acid is typically removed at the top of the column, while the polymethylol compound can generally be discharged from the column bottom.

In a preferred embodiment, the distillation is therefore preferably carried out as follows:

The condenser is generally operated at a temperature at which the predominant portion of the low boilers is condensed at the corresponding top pressure.

In general, the operating temperature of the condenser is in the range from 0 to 80° C., preferably 20 to 50° C.

The cooling medium used here may preferably be very cold water (e.g. about 5° C.) or a coolant mixture (e.g. glycol-water at, for example, −20° C.).

The top pressure is more preferably 0.001 to 0.9 bar, more preferably 0.01 to 0.5 bar. On the industrial scale, the vacuum is typically obtained by means of a steam ejector. In the column bottom, preference is given to establishing a temperature which is above the evaporation temperature of the polymethylol formate, such that the polymethylol formate is converted completely or very substantially completely to the gas phase.

Particular preference is given to establishing a temperature which is 5% to 50% above the boiling temperature of the polymethylol formate and most preferably 10% to 20% above the boiling temperature of the polymethylol formate.

For example, in the case of preparation of NPG using TMA as the tertiary amine and a pressure at the top of the column of 175 mbar, a column bottom temperature of preferably 150 to 170° C., more preferably of 160 to 165° C., can be established.

The reflux at the top of the column is generally adjusted such that the predominant amount of the polymethylol formate is retained in the column.

The condensate obtained at the condenser is preferably recycled into the distillation column to an extent of more than 20% by weight, preferably to an extent of more than 30% by weight. The condensate is preferably recycled into the top of the column.

The energy required for the evaporation is typically introduced by means of an evaporator in the column bottom.

The evaporator is typically a natural circulation evaporator or forced circulation evaporator. However, it is also possible to use evaporators with a short residence time, falling film evaporators, helical tube evaporators, wiped film evaporators or a short path evaporator. The evaporator can be supplied with heat in a suitable manner, for example with 16 bar steam or heat carrier oil.

The distillation column preferably has internals for increasing the separating performance. The distillative internals may, for example, be present as a structured packing, for example as a sheet metal packing such as Mellapak 250 Y or Montz Pak, B1-250 type. It is also possible for a structured packing with relatively low or increased specific surface area to be present, or it is possible to use a fabric packing or a structured packing with another geometry, such as Mellapak 252Y. What are advantageous in the case of use of these distillative internals are the low pressure drop and the low specific liquid holdup compared to, for example, valve trays. The internals may be present in one or more sections.

The discharge from the hydrogenation is preferably fed in within a spatial region between ¼ and ¾ of the theoretical plates of the distillation column, more preferably in a spatial region between ⅓ and ⅔ of the theoretical plates of the distillation column. For example, the feed may be somewhat above the middle of the theoretical plates (ratio 3:4).

The number of theoretical plates is generally in the range from 5 to 30, preferably 10 to 20.

The condensate obtained in the condenser is a mixture of low boilers which is fed to the column as described above, predominantly as reflux. For example, the low boiler mixture may comprise tertiary amine, methylolalkanal of the formula (II), unconverted aldehyde, water and alcohols of the formula (III), such as isobutanol from isobutyraldehyde or n-butanol from n-butyraldehyde, and methanol from formaldehyde.

According to the invention, components are recovered from the low boiler mixture which is obtained in the distillation of hydrogenation discharges from the preparation of polymethylols,
by multistage distillation of the low boiler mixture comprising a tertiary amine, water, methanol, polymethylol of the formula (I)

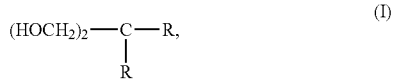

methylolalkanal of the formula (II)

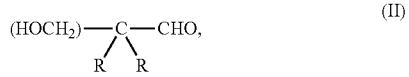

alcohol of the formula (III)

and an alkanal with a methylene group in the α position to the carbonyl group,
and in which each R is independently a further methylol group or an alkyl group having 1 to 22 carbon atoms or an aryl or aralkyl group having 6 to 22 carbon atoms, a first distillation stage involving separating the low boiler mixture into a higher-boiling, predominantly water-rich fraction and into a lower-boiling aqueous organic fraction comprising the tertiary amine,
and the second distillation stage involving separating the aqueous organic fraction from the first distillation stage into a predominantly amine-containing fraction and a further amine-depleted fraction,
wherein the tertiary amine is trimethylamine or triethylamine, and the bottom temperature in the second distillation stage is 110° C. and more.

The low boiler mixture which is used in the process according to the invention comprises preferably
1 to 30% by weight of methanol,
0.01 to 1% unconverted aldehyde, (alkanal with a methylene group in the α position to the carbonyl group)
0.1 to 5% by weight of alcohol (III),
0.1 to 5% by weight of tertiary amine,
0.01 to 5% by weight of methylolalkanal (II),
0 to 5% by weight of organic secondary compounds,
remainder water.

The low boiler mixture more preferably comprises
1 to 20% by weight of methanol,
0.01 to 1% unconverted aldehyde, (alkanal with a methylene group in the α position to the carbonyl group)
0.5 to 5% by weight of alcohol (III),
0.5 to 5% by weight of tertiary amine,
0.01 to 1% by weight of methylolalkanal (II),
0 to 5% by weight of organic secondary compounds,
remainder water.

Such a low boiler mixture is preferably obtained by multistage reaction of alkanals with formaldehyde.

The low boiler mixture is preferably obtained by the hydrogenation process.

However, it is also possible to perform the process according to the invention for distilling a low boiler mixture with a low boiler mixture which has been obtained by organic Canizzaro reaction.

As described above, such a low boiler mixture is preferably obtained in a multistage hydrogenation process involving, in stage a), condensing alkanals with formaldehyde in the presence of tertiary amines as a catalyst to give methylolalkanals of the formula (II), and then, in stage b), distillatively separating the reaction mixture obtained from stage a) into bottoms comprising predominantly compounds of the formula (II), and a top stream comprising low boilers, and, in stage c), hydrogenating the bottom discharge from stage b) and then, in a stage d), distilling the discharge from stage c), the low boiler mixture being removed from stage d).

In a preferred embodiment, a base is added to the low boiler mixture before it is fed into the first distillation stage.

Examples of bases used are alkali metal hydroxides such as LiOH, NaOH or KOH.

Preference is given to adding NaOH, more preferably a 25% aqueous NaOH solution. The concentration of the base metered in is generally in the range from 0.01 to 2% by weight, preferably in the range from 0.5 to 1% by weight, more preferably in the range from 0.2 to 0.4% by weight.

The addition of the base generally splits the formate adduct (adduct of tertiary amine and formic acid) present in the condensate stream into free amine and sodium formate. This measure allows the yield of tertiary amine recovered to be increased further.

According to the invention, the low boiler mixture is fed to a multistage distillation. The configuration of the multistage distillation generally depends on the boiling point of the tertiary amine used.

Trimethylamine has a boiling point at atmospheric pressure of approx. 3° C., which is lower than the boiling point of methanol (65° C.).

When TMA is used as the tertiary amine, the low boiler mixture is generally distilled in three stages.

In the first distillation stage ("low boiler distillation"), the low boiler mixture is generally separated into an aqueous organic fraction which is withdrawn at the top of the column, and a predominantly water-rich fraction which is discharged from the column bottom.

The aqueous discharge from the column bottom, which generally comprises alkali metal formate which has been formed by addition of alkali metal hydroxides is generally sent to a biological wastewater treatment.

The aqueous organic fraction comprising methylolalkanal of the formula (II), alcohol of the formula (III), tertiary amine, methanol, unconverted aldehyde and residues of water is generally separated in a second distillation stage ("TMA distillation") by distillation into a predominantly amine-containing fraction ("TMA fraction") which can be withdrawn at the top of the column, and an aqueous organic (amine-depleted) fraction which comprises methanol, water and alcohol of the formula (III).

According to the invention, the "TMA distillation" is performed in such a way that the bottom temperature during the distillation is 110° C. and more.

The amine obtained at the top of the column of the second distillation stage comprises preferably less than 2% by weight and more preferably less than 1% by weight of by-products such as methanol. The TMA thus obtained can be recycled into the process, for example into the first stage of the hydrogenation process (stage a), aldol reaction) and can thus be used as a basic catalyst in the aldol reaction.

The aqueous organic fraction from the bottom of the second distillation stage ("TMA distillation") is generally separated in a third distillation stage ("MeOH distillation") into a methanolic phase which can be withdrawn at the top of the column, and an aqueous organic fraction which is discharged from the column bottom.

The methanolic phase comprises predominantly methanol and preferably less than 2% by weight, more preferably less than 1% by weight, of other secondary components.

The aqueous organic phase discharged at the bottom of the column is generally cooled in a heat exchanger to approx. 20 to 50° C., preferably 25 to 35° C., and collected in a phase separator. In the phase separator, a separation is typically effected into an organic phase which comprises predominantly alcohol of the formula (III), and may comprise small proportions of methanol, water and other organic components. The aqueous solution removed in the phase separator is generally sent to biological wastewater treatment or recycled into the first distillation stage. The organic phase removed in the phase separator is generally likewise discharged and generally sent to incineration.

The "low boiler distillation" is preferably performed under the following conditions:

The condensate obtained in the condenser is preferably recycled into the distillation column to an extent of more than 10% by weight, more preferably to an extent of more than 50% by weight. The condensate is preferably recycled into the top of the column.

The condenser is operated at a temperature in the range from 5 to 40° C., preferably 25 to 35° C., especially 30° C.

The top pressure is preferably in the range from 0.8 to 1.2 bar, more preferably 0.9 to 1.1 bar and especially preferably 1.02 to 1.08 bar.

The cooling medium used here may preferably be very cold water (e.g. about 5° C.) or a coolant mixture (e.g. glycol-water at, for example, −20° C.).

On the industrial scale, the vacuum is typically obtained by means of a steam ejector or of a commercial waterjet pump.

The temperature of the column bottom is in the region of the boiling temperature of water at the appropriate pressure. It may be just below or else just above the boiling temperature of water. The temperature of the column bottom is preferably 80 to 110% of the boiling temperature of water, more preferably 90 to 108% and most preferably 95 to 105%.

For example, at a top pressure of 1.05 bar, a temperature of the column bottom of 105° C. can advantageously be established.

The energy required for the evaporation is typically introduced by means of an evaporator in the column bottom.

The evaporator is preferably a natural circulation evaporator or forced circulation evaporator. However, it is also possible to use evaporators with short residence time, falling film evaporators, helical tube evaporators, wiped film evaporators or a short path evaporator.

The distillation column preferably has internals for increasing the separating performance.

The distillative internals may be present, for example, as a structured packing, for example as a sheet metal packing such as Mellapak 250 Y or Montz Pak, B1-250 type. It is also possible for a structured packing with relatively low or increased specific surface area to be present, or it is possible to use a fabric packing or a structured packing with another geometry such as Mellapak 252 Y. It is equally possible to install valve trays.

The internals may be divided into one or more sections.

The condensate stream from the hydrogenation feed distillation is preferably fed in within a spatial region between ¼ and ¾ of the theoretical plates of the distillation column, more preferably in a spatial region between ⅓ and ⅔ of the theoretical plates of the distillation column, preferably at ⅔ of the theoretical plates. When, for example, the column packing is divided into three sections, the feed may advantageously be above the 2nd section.

The number of theoretical plates is generally in the range from 5 to 30, preferably 10 to 20.

An discharge is preferably discharged from the bottom of the evaporator, which comprises predominantly water, and if appropriate alkali metal formate which has been formed by addition of alkali metal hydroxides. The bottom discharge from the "low boiler distillation" is generally sent to a biological wastewater treatment.

In the condenser, a condensate is typically obtained, which comprises water, methanol, unconverted aldehyde, TMA and alcohol of the formula (III), which is fed to the "TMA distillation" as the top product.

The "TMA distillation" is preferably performed under the following conditions:

The condensate obtained in the condenser is preferably recycled into the distillation column to an extent of more than 30% by weight, more preferably to an extent of more than 50% by weight. The condensate is preferably recycled into the top of the column.

The condenser is operated at a temperature in the range from 20 to 40° C., preferably 25 to 35° C., especially 30° C.

The cooling medium used here may preferably be very cold water (e.g. about 5° C.) or a coolant mixture (e.g. glycol-water at, for example, −20° C.).

The top pressure is preferably in the range from 3 to 10 bar, more preferably 4 to 8 bar and especially preferably 6 bar absolute, i.e. 5 bar gauge.

The temperature of the column bottom is, according to the invention, 110° C. and more.

The temperature of the column bottom is preferably 110 to 160° C., more preferably 110 to 145° C. and most preferably 130 to 145° C.

For example, at a top pressure of 6 bar, a temperature of the column bottom of 140° C. can advantageously be established.

The energy required for the evaporation is typically introduced into the column bottom by an evaporator.

The evaporator is preferably a natural circulation evaporator or forced circulation evaporator. However, it is also possible to use evaporators with a short residence time, falling film evaporators, helical tube evaporators, wiped film evaporators or a short path evaporator.

The "TMA distillation" is preferably performed in a tray column.

Tray columns are used for a multitude of mass transfer processes between liquids and gases. A liquid is conducted from the top downward in countercurrent to a gas phase. The gas which flows through orifices in the column trays is fed into the liquid such that intensive mass transfer takes place. The liquid is passed on to the column tray below in each case either by means of specific drain devices, especially tray shafts (in the case of crossflow trays) or by means of orifices in the column trays (in the case of dual-flow trays). Examples of different tray types are sieve trays, dual-flow trays, bubble-cap trays or valve trays. The trays are found to be advantageous in the case of the reaction of the aldehyde, since they possess high liquid holdups.

The number of actual plates is generally in the range from 10 to 100, preferably 20 to 90, more preferably 30 to 40.

In a very particularly preferred embodiment, the number of trays is selected such that the residence time in the column is 5 minutes and more, preferably 7 minutes and more and more preferably 10 minutes and more.

The residence time is preferably in the range from 5 to 45 minutes, preferably in the range from 7 to 30 minutes and more preferably in the range from 8 to 20 minutes. According to the disclosure, the residence time in the column is calculated by dividing the volume of the liquid holdup of the separating internals between the bottom and feed ($V_{holdup}$) by the sum of reflux and feed volume flow of the column (residence time=$V_{holdup}$/(feed stream+reflux stream)).

When, for example, the separating internals are trays, as is the case in the preferred embodiment described above, the volume of the liquid holdup of the separating internals between bottom and feed is typically the liquid volume on the corresponding trays.

In the context of the present invention, the volume $V_{holdup}$ may also comprise the volume of the column bottom ($V_{bottom}$) and/or the volume of an upstream thermal reactor $V_{thermal\ reactor}$ when the temperature of the liquid in these volumes is 110° C. and more. In the context of this invention, it has been found that a further improvement in the removal of the tertiary amine is possible when the residence time at high temperatures is sufficiently long. This is probably attributable to the fact that the aldehydes unconverted in the aldol reaction reduce the volatility of the tertiary amines and thus complicate the removal. A possible explanation for the improved removal is that, at the inventive temperature of 110° C. and more, the aldehydes react to give higher-boiling by-products which no longer hinder the removal of the tertiary amine. Thus, instead of increasing the residence time in the hot part of the column, for example by increasing the liquid volume of the separating internals (higher volume per tray or increasing the number of trays), the residence time can also be prolonged by connecting a thermal reactor upstream of the distillation column or enlarging the column bottom.

In a further particularly preferred embodiment, the residence time at temperatures of 110° C. and more in the second distillation stage is therefore preferably 5 minutes and more and more preferably 10 minutes and more.

The residence time at temperatures of 110° C. and more in the second distillation stage is preferably in the range from 5 to 45 minutes, preferably in the range from 7 to 30 minutes and more preferably in the range from 10 to 20 minutes.

In this preferred embodiment, the residence time is defined as the liquid volume of the second column which has a temperature of 110° C. and more ($V_{liquid}$) divided by the sum of reflux and feed volume flow of the column (residence time=$V_{liquid}$/(feed stream+reflux stream)), where the liquid volume of the second column ($V_{liquid}$) is the sum of $V_{holdup}$, $V_{thermal\ reactor}$ and $V_{bottom}$ ($V_{liquid}=V_{holdup}+V_{thermal\ reactor}+V_{bottom}$). In this particularly preferred embodiment comprises by definition only the liquid volumes which have a temperature of 110° C. and more. Liquid volumes which have a temperature of less than 110° C. are not considered for the calculation of the residence time in this particularly preferred embodiment.

The discharge from the "low boiler distillation" is preferably fed in within a spatial region between ¼ and ¾ of the actual plates of the distillation column, more preferably within a spatial region between ⅓ and ⅔, preferably between ½ and ⅔, of the actual plates of the distillation column, preferably at ⅔ of the actual plates. For example, in a column with 60 actual plates, the feed is preferably above the 35th tray from the bottom.

In an alternative embodiment, the distillation column has internals for increasing the separating performance.

The distillative internals may, for example, be present as a structured packing, for example as a sheet metal packing such as Mellapak 250 Y or Montz Pak, B1-250 type. It is also possible for a structured packing with relatively low or increased specific surface area to be present, or it is possible to use a fabric packing or a structured packing with another geometry such as Mellapak 252 Y. The internals may be divided into one or more sections.

In the condenser, a condensate is typically obtained, which comprises predominantly TMA, preferably with less than 2% by weight, more preferably with less than 1% by weight, of by-products such as methanol. The TMA thus obtained can be recycled into the polymethylol preparation, for example into the first stage of the hydrogenation process (stage a), aldol reaction).

Preferably, an aqueous organic discharge is discharged from the bottom of the evaporator, which comprises methylolalkanal of the formula (II), alcohol of the formula (III), methanol, traces of aldehyde and water.

The bottom discharge is generally fed to the "MeOH distillation".

The "MeOH distillation" is preferably performed under the following conditions:

The condensate obtained in the condenser is preferably recycled into the distillation column to an extent of more than 30% by weight, more preferably to an extent of more than 50% by weight. The condensate is preferably recycled into the top of the column.

The condenser is operated at a temperature in the range from 20 to 40° C., preferably 25 to 35° C., especially 30° C.

The cooling medium used here may preferably be very cold water (e.g. about 5° C.) or a coolant mixture (e.g. glycol-water at, for example, −20° C.).

The top pressure is preferably in the range from 0.8 to 1.2 bar, more preferably 0.9 to 1.1 bar and especially preferably 1.02 to 1.08 bar.

On the industrial scale, the vacuum is typically obtained by means of a steam ejector or of a commercial waterjet pump.

The temperature of the column bottom is generally adjusted such that methanol is converted to the gaseous state.

The temperature of the column bottom is preferably 100 to 300% of the boiling temperature of methanol, more preferably 100 to 175% and most preferably 110 to 150%.

For example, at a top pressure of 1.05 bar, preference may be given to establishing a temperature of the column bottom of 92° C., the temperature corresponding to a value of approx. 150% of the boiling temperature of methanol at this pressure.

The energy required for the evaporation is typically introduced by means of an evaporator in the column bottom.

The evaporator is preferably a natural circulation evaporator or a forced circulation evaporator. However, it is also possible to use evaporators with a short residence time, falling film evaporators, helical tube evaporators, wiped film evaporators or a short path evaporator.

The distillation column preferably has internals for increasing the separating performance.

The distillative internals may, for example, be present as a structured packing, for example as a sheet metal packing such as Mellapak 250 Y or Montz Pak, B1-250 type. It is also possible for a structured packing with relatively low or increased specific surface area to be present, or it is possible to use a fabric packing or a structured packing with another geometry such as Mellapak 252 Y. What are advantageous in the case of use of these distillative internals are the low pressure drop and the low specific liquid holdup compared to, for example, valve trays.

The internals may be divided into one or more sections.

The bottom stream from the "TMA distillation" is preferably fed in within a spatial region between ¼ and ¾ of the actual plates of the distillation column, more preferably within a spatial region between ⅓ and ⅔ of the actual plates of the distillation column, preferably at ⅔ of the actual plates. When, for example, the column packing is divided into three sections, the feed may advantageously be above the 2nd section.

The number of actual plates is generally in the range from 5 to 50, preferably 20 to 30.

In the condenser, a condensate (methanolic phase) is typically obtained. The methanolic phase comprises predominantly methanol and preferably less than 2% by weight, more preferably less than 0.15% by weight, of other secondary components. The methanolic phase thus obtained can be used as a starting material or solvent in organic syntheses.

Preferably, an aqueous organic phase is discharged from the bottom of the evaporator, which comprises predominantly alcohol of the formula (III), and may comprise small proportions of methanol, water and other organic components.

The aqueous organic phase discharged at the bottom of the column is generally cooled in a heat exchanger to approx. 20 to 50° C., preferably 25 to 35° C., and collected in a phase separator. In the phase separator, a separation is typically effected into an organic phase and an aqueous phase.

The aqueous solution removed in the phase separator is generally sent to biological wastewater treatment or recycled into "low boiler distillation".

The organic phase removed in the phase separator is generally likewise discharged and is generally sent to incineration.

In a particular embodiment, the "TMA distillation" and the "MeOH distillation" are performed in a single stage together in one dividing wall column.

In a dividing wall column, a dividing wall is typically arranged in the longitudinal direction of the column to form an upper common column region, a lower common column region, a feed part with rectifying section and stripping section, and a withdrawal part with rectifying section and stripping section.

The construction of a typical dividing wall column is described, for example, in EP 0122 367.

The dividing wall column is preferably configured as a tray column.

The number of actual plates is generally between 20 and 100, preferably between 30 and 80 and preferably between 50 and 70.

The dividing wall runs typically above the first quarter of the actual plates to above the third quarter of the actual plates. In the case of 60 actual plates, for example, the dividing wall runs preferably from the 15th to the 45th plate.

The top product from the "low boiler distillation" is introduced on the feed side of the dividing wall column, preferably within a region between ⅓ and ⅔ of the total number of actual plates, preferably at the level of half of the actual plates.

The distillation is preferably performed at elevated pressure, preferably at a pressure of 1 to 10 bar, preferably 2 to 8 bar, more preferably 3 to 7 bar, especially 5 bar.

According to the invention, the temperature of the column bottom is 110° C. and more. The temperature of the column bottom is preferably 110 to 160° C., more preferably 110 to 145° C. and most preferably 120 to 140° C.

For example, at a top pressure of 5 bar, a temperature of the column bottom of 130° C. can advantageously be established.

The energy required for the evaporation is typically introduced by means of an evaporator in the column bottom.

The evaporator is preferably a natural circulation evaporator or forced circulation evaporator. However, it is also possible to use evaporators with short residence time, falling film evaporators, helical tube evaporators, wiped film evaporators or a short path evaporator.

The condenser is operated at a temperature in the range from 20 to 40° C., preferably 25 to 35° C., especially 30° C.

The cooling medium used here may preferably be very cold water (e.g. about 5° C.) or a coolant mixture (e.g. glycol-water at, for example, −20° C.).

The condensate obtained in the condenser is preferably recycled into the distillation column to an extent of more than 30% by weight, more preferably to an extent of more than 50% by weight, especially preferably more than 75% by weight. The recycled condensate is preferably divided into 10 to 50% to the feed side and into 50 to 90% to the withdrawal side.

In a very particularly preferred embodiment, the residence time in the column is 5 minutes and more, preferably 7 minutes and more and more preferably 10 minutes and more.

The residence time is preferably in the range from 5 to 45 minutes, preferably in the range from 7 to 30 minutes and more preferably in the range from 8 to 20 minutes. According to the disclosure, the residence time in the dividing wall column is calculated by dividing the volume of the liquid holdup of the separating internals below the lower end of the dividing wall and above the bottom ($V_{holdup}$) by the sum of reflux and feed volume flow of the column (residence time=$V_{holdup}$/(feed stream+reflux stream)).

When, for example, the separating internals are trays, as is the case in the preferred embodiment described above, the volume of the liquid holdup of the separating internals between bottom and feed is typically the liquid volume on the corresponding trays.

In the context of the present invention, the volume $V_{holdup}$ may also comprise the volume of the column bottom ($V_{bottom}$) and/or the volume of an upstream thermal reactor $V_{thermal\ reactor}$ when the temperature of the liquid in these volumes is 110° C. and more. In the context of this invention, it has been found that a further improvement in the removal of the tertiary amine is possible when the residence time at high temperatures is sufficiently long. This is probably attributable to the fact that the aldehydes unconverted in the aldol reaction reduce the volatility of the tertiary amines and hence complicate the removal. One possible explanation for the improved removal is that, at the inventive temperature of 110° C. and more, the aldehydes react to give higher-boiling by-products which no longer hinder the removal of the tertiary amine.

It is thus possible, instead of increasing the residence time in the hot part of the column, for example by increasing the liquid volume of the separating internals (higher volume per tray or increasing the number of trays), also to prolong the residence time by connecting a thermal reactor upstream of the distillation column or enlarging the column bottom.

In a further particularly preferred embodiment, the residence time at temperatures of 110° C. and more in the second distillation stage is therefore preferably 5 minutes and more and more preferably 10 minutes and more.

Preferably, the residence time at temperatures of 110° C. and more in the second distillation stage is in the range from 5 to 45 minutes, preferably in the range from 7 to 30 minutes and more preferably in the range from 10 to 20 minutes.

In this preferred embodiment, the residence time is defined as the liquid volume of the second column which has a temperature of 110° C. and more ($V_{liquid}$) divided by the sum of reflux and feed volume flow of the column (residence time=$V_{liquid}$/(feed stream+reflux stream)), where the liquid volume of the second column ($V_{liquid}$) is the sum of $V_{holdup}$, $V_{thermal\ reactor}$ and $V_{bottom}$ ($V_{liquid}\ V_{holdup}\ V_{thermal\ reactor}$+$V_{bottom}$). In this particularly preferred embodiment comprises comprises by definition only the liquid volumes which have a temperature of 110° C. and more. Liquid volumes which have a temperature of less than 110° C. are not considered for the calculation of the residence time in this particularly preferred embodiment.

The condensate withdrawn at the top of the column comprises predominantly TMA, preferably to an extent of more than 95% by weight, more preferably to an extent of more than 98% by weight, of TMA. Methanol may be present as a secondary component.

The TMA thus obtained can be recycled into the first stage of the hydrogenation process (stage a), aldol reaction).

On the withdrawal side, a methanolic fraction is withdrawn.

The methanolic fraction is preferably withdrawn in a spatial region between ⅙ and ½, preferably ⅕ and ⅓, especially ¼ and ⅓, of the actual plates of the distillation column. The methanolic fraction comprises preferably more than 99% by weight of methanol, more preferably more than 99.5% by weight of methanol and most preferably more than 99.8% by weight of methanol.

An aqueous organic phase is generally discharged from the column bottom, and comprises predominantly alcohol of the formula (III), and may comprise small proportions of methanol, water and other organic components.

The aqueous organic phase discharged at the column bottom is generally cooled in a heat exchanger to approx. 20 to 50° C., preferably 25 to 35° C., and collected in a phase separator. In the phase separator, a separation is typically effected into an organic phase and an aqueous phase. The aqueous solution removed in the phase separator is generally sent to biological wastewater treatment or recycled into the first distillation stage ("low boiler distillation").

The organic phase removed in the phase separator is generally likewise discharged and is generally sent to incineration.

When TEA is used as the tertiary amine, the low boiler mixture is generally likewise distilled in three stages. At atmospheric pressure, TEA has a boiling point of approx. 89° C., which is below the boiling point of water (100° C.) but above the boiling point of methanol (approx. 65° C.).

The low boiler mixture is generally worked up by distillation in three stages.

In the first distillation stage ("low boiler distillation"), the low boiler mixture is generally separated into an aqueous organic fraction which is withdrawn at the top of the column, and a predominantly water-rich fraction which is discharged from the column bottom.

The aqueous discharge from the column bottom, which generally comprises alkali metal formate which has been formed through addition of alkali metal hydroxides, is generally sent to biological wastewater treatment.

The aqueous organic fraction comprising methylolalkanal of the formula (II), alcohol of the formula (III), TEA, methanol, unconverted aldehyde and water is generally separated in a second distillation stage ("TEA distillation") by distillation into a predominantly amine-containing fraction ("TEA fraction") which comprises the majority of the MeOH and can be withdrawn at the top of the column, and an aqueous organic (amine-depleted) fraction which comprises predominantly water and alcohol of the formula (III), and residues of MeOH.

According to the invention, the "TEA distillation" is performed such that the bottom temperature during the distillation is 100° C. and more.

The amine obtained at the top of the column comprises relatively large amounts of MeOH; the proportion of MeOH in the condensate is preferably in the range from 30 to 90% by weight, more preferably in the range from 40 to 85% by weight and especially preferably 50 to 75% by weight.

The top product from the second distillation stage ("TEA distillation") is generally separated in a third distillation stage ("MeOH distillation") into a methanolic phase which can be withdrawn at the top of the column, and a fraction which comprises TEA, which can be discharged from the column bottom.

The methanolic phase comprises predominantly methanol and preferably less than 3% by weight, more preferably less than 2% by weight, especially preferably less than 1% by weight, of other secondary components.

The first stage ("low boiler distillation") is preferably performed under the same conditions as have been described in the "low boiler distillation" in the case of use of TMA.

The second stage ("TEA distillation") is preferably performed under the same conditions as have been described above in the "TMA distillation".

Under these conditions, a condensate is typically obtained in the condenser, which comprises predominantly MeOH and TEA, and residues of water.

Typically, the proportion of MeOH in the condensate is in the range from 30 to 90% by weight, more preferably in the range from 40 to 85% by weight and especially preferably 50 to 80% by weight.

The proportion of TEA is preferably 10 to 70% by weight, more preferably 15 to 60% by weight, especially preferably 20 to 50% by weight.

The proportion of water is typically less than 10% by weight, preferably less than 6% by weight and more preferably less than 4% by weight.

A stream is discharged from the bottom of the evaporator and comprises, as well as water, generally alcohol of the formula (III). This stream is preferably cooled and separated in a phase separator into an organic phase which comprises predominantly the alcohol of the formula (III), and an aqueous phase.

The condensate stream from the second stage ("TEA distillation") is preferably fed to a third stage ("MeOH distillation").

The "MeOH distillation" is preferably performed under the following conditions:

The condensate obtained in the condenser is preferably recycled into the distillation column to an extent of more than 30% by weight, more preferably to an extent of more than 50% by weight. The condensate is preferably recycled into the top of the column.

The condenser is operated at a temperature in the range from 20 to 40° C., preferably 25 to 35° C., especially 30° C.

The cooling medium used here may preferably be very cold water (e.g. about 5° C.) or a coolant mixture (e.g. glycolwater at, for example, −20° C.).

The top pressure is preferably in the range from 0.8 to 1.2 bar, more preferably 0.9 to 1.1 bar and especially preferably 1.02 to 1.08 bar.

On the industrial scale, the vacuum is obtained typically by means of a steam ejector or of a commercial waterjet pump.

The temperature of the column bottom is generally adjusted such that methanol is converted to the gaseous state.

The temperature of the column bottom is preferably 100 to 300% of the boiling temperature of methanol, more preferably 100 to 175% and most preferably 105 to 150%.

For example, at a top pressure of 1.05 bar, a temperature of the column bottom of 75° C. can preferably be established, the temperature corresponding to a value of approx. 115% of the boiling temperature of methanol at this pressure.

The energy required for the evaporation is typically introduced by means of an evaporator in the column bottom.

This evaporator is preferably a natural circulation evaporator or forced circulation evaporator. However, it is also possible to use evaporators with a short residence time, falling film evaporators, helical tube evaporators, wiped film evaporators or a short path evaporator.

The distillation column preferably has internals for increasing the separating performance.

The distillative internals may, for example, be present as a structured packing, for example as a sheet metal packing such as Mellapak 250 Y or Montz Pak, B1-250 type. It is also possible for a structured packing with relatively low or increased specific surface area to be present, or it is possible to use a fabric packing or a structured packing with another geometry such as Mellapak 252 Y. What are advantageous in the case of use of these distillative internals are the low pressure drop and the low specific liquid holdup compared, for example, to valve trays.

The internals may be divided into one or more sections.

The bottom stream from the "TMA distillation" is preferably fed in within a spatial region between ¼ and ¾ of the actual plates of the distillation column, more preferably within a spatial region between ⅓ and ⅔ of the actual plates of the distillation column, preferably at ⅔ of the actual plates. When, for example, the column packing is divided into three sections, the feed may advantageously be above the 2nd section.

The number of actual plates is generally in the range from 5 to 50, preferably 20 to 30.

In the condenser, a condensate is typically obtained, which comprises predominantly methanol. The methanolic phase comprises predominantly methanol and preferably less than 2% by weight, more preferably less than 0.15% by weight, of other secondary components. The methanolic phase thus obtained can be used as a starting material or solvent in organic syntheses.

Preferably a residue is discharged from the bottom of the evaporator, which comprises predominantly TEA, and small proportions of methanol, water and other organic components.

The TEA content in the bottom discharge is preferably more than 60% by weight, preferably more than 70% by weight and more preferably more than 80% by weight.

The TEA discharged at the bottom of the column is generally cooled in a heat exchanger to approx. 10 to 50° C., preferably 15 to 25° C., and collected in a phase separator. In the phase separator, a separation is typically effected into an organic phase which comprises predominantly TEA and an aqueous methanolic phase. The aqueous methanolic phase can be discarded or sent to biological wastewater treatment.

The TEA phase removed in the phase separator is generally recycled into the aldol reaction.

Inventive separation of the by-products and products obtained, more particularly the recyclability of the tertiary amine into the aldol reaction, allows the economic viability of the process to be improved further, since most of the components can be utilized in material form, for example by recycling into the process. The proportion of compounds which have to be sent to disposal is reduced, such that the disposal costs in the process according to the invention can be reduced.

The tertiary amine recovered in the inventive distillative workup of the low boiler mixture can be recycled as a catalyst into the polymethylol preparation, for example into the aldol reaction (reaction of formaldehyde with aldehydes), since it comprises only a low proportion of alcohols, such as methanol or n-butanol. Specifically these alcohols are disadvantageous for the recyclability, since these alcohols enter into side reactions in the aldol reaction, which reduce the yield. Moreover, such alcohols are troublesome in the subsequent removal of unconverted aldehydes from the discharge of the aldol reaction, since they have similar boiling points and can form azeotropes with the unconverted aldehydes and/or the hemiacetals which hinder separation. The process according to the invention very substantially avoids these disadvantages.

There is thus no accumulation of methanol in the aldol reaction.

The other components of the low boiler mixture, such as MeOH, can likewise be obtained in a high purity, such that the utilization of this substance is possible, for example as a starting material or solvent for organic syntheses, such as formaldehyde preparation.

In addition, it was possible to keep the apparatus complexity for the distillation as low as possible, in order to provide an economically viable workup process.

The invention is illustrated by the following examples:
Preparation of Crude Polymethylol by the Hydrogenation Process
Stage a) Aldol Reaction:

Approx. 750 g/h of isobutyraldehyde (approx. >99.5 GC area % of IBA) were reacted with approx. 700 g/h of formaldehyde (approx. 49% by weight of formaldehyde, 1.5% by weight of methanol, remainder water) and 40 g/h of trimethylamine solution (50% by weight of TMA in water) in a two-stage stirred tank cascade.

Stage b) Distillative Separation of the Reaction Mixture from Stage a):

Subsequently, the reaction discharge from the aldol reaction was freed of low boilers by distillation in a column. The column was equipped with 1.5 m of fabric packing (specific surface area 500 m$^2$/m$^3$) in the rectifying section and 4 m of sheet metal packing (250 m$^2$/m$^3$). The aldolization discharge was fed in above the sheet metal packing. At the top of the column, a condenser with cooling water (approx. 10° C.) and a downstream phase separator was used. At the top, the distillate was fed to the condenser in gaseous form. Approx. 255 g/h of liquid condensate were obtained. In the phase separator connected downstream, an aqueous phase of 95 g/h was removed and fed completely to the column. In addition, 135 g/h were fed from the phase separator to the first stirred tank of the stirred tank cascade of the aldol reaction. In order to maintain the regulation temperature in the column at 85° C., 25 g/h of organic phase were additionally fed to the column. In the cold trap connected downstream of the condenser, approx. 1 g/h of liquid was obtained (approx. 80% by weight of isobutyraldehyde (IBA), approx. 20% by weight of TMA), which was likewise recycled. The IBA removal was conducted at a top pressure of approx. 1 bar absolute. The evaporator used was a falling film evaporator. A bottom temperature in the bottom of the column of 104° C. was established. The reflux rate (i.e. cooling water rate of the partial condenser) to the column was regulated by means of the temperature in the middle of the fabric packing; a temperature of 85° C. was established.

By means of a pump, approx. 100 kg/h of liquid were drawn off from the bottom of the column. This was fed to the falling film evaporator (consisting of an oil-heated stainless steel tube, length 2.5 m, internal diameter approx. 21 mm, wall thickness approx. 2 mm). Approx. 1.5 kg/h of product with a concentration of approx. 0.3% by weight of isobutyraldehyde were drawn off from the bottom of the falling film evaporator. The vapors and excess liquid were fed to the bottom of the column. The bottom product discharged comprised approx. 70% by weight of HPA, approx. 1.5% by weight of HPN, 0.3% by weight of isobutyraldehyde (IBA), remainder water.

Stage c) Hydrogenation of the Bottom Discharge from Stage b):

The resulting bottom product was subsequently subjected to a hydrogenation by means of a fixed bed.

The catalyst was activated as follows:

150 ml of a Cu/Al$_2$O$_3$ catalyst as described in EP 44444 were activated in a tubular reactor at 190° C. by passing over a mixture of 5% by volume of hydrogen and 95% by volume of nitrogen (total volume 50 l (STP)/h) at ambient pressure for 24 hours.

The hydrogenation was performed as follows:

The starting solution used was the mixture described above as hydrogenation feed. Approx. 10% by weight based on the hydrogenation feed of a 15% by weight aqueous solution of trimethylamine was added to the mixture. The feed thus obtained was conducted in trickle mode at H$_2$ pressure 40 bar through the reactor heated to 120° C. The space velocity was 0.4 kg of HPA/(l$_{cat.}$*h). A portion of the hydrogenation discharge was added again to the feed (circulation mode). The ratio of circulation to feed was 10:1. The pH of samples of the reactor discharge at room temperature was measured at 8.9.

The composition of the aqueous polymethylol mixture from stage c) was:
NPG: 69% by weight
Methanol: 3.5% by weight
TMA: 2% by weight
organic secondary compounds (HPS, isobutanol): <2% by weight
TMA formate: 1% by weight
Water: 23% by weight Stage d): Distillation of the Aqueous Polymethylol Mixture from Stage c):

The resulting discharge (approx. 1.5 kg/h) was fed to a distillative separation. A packed column (DN 50 mm) with three sequences of structured sheet metal packing each of length 1 m and specific surface area 500 m$^2$/m$^3$ was used. The feed was above the lowermost sequence. A top pressure of approx. 175 mbar absolute was established. In the bottom, a temperature of 160 to 165° C. was established; the energy was supplied to the column by means of a natural circulation evaporator. The vapors obtained at the top were fed to a condenser; this precipitates the vapors obtained virtually completely at 30° C. The vacuum was obtained by means of a simple commercial waterjet vacuum pump. Approx. 350 g/h of the distillate obtained ("low boiler mixture") were discharged; approx. 250 g/h were metered into the column at the uppermost packing section as reflux. The water used to obtain the vacuum was sent to biological wastewater treatment.

The low boiler mixture from stage d) had the following composition:
11% by weight of methanol,
0.1% by weight of unconverted aldehyde,
0.5% by weight of NPG,
1.5% by weight of tertiary amine,
1% TMA formate
0.1% by weight of methylolalkanal (II),
4% isobutanol, alcohol (III),
remainder organic secondary compounds,
approx. 80% residual water.

EXAMPLE 1

Distillation of the Low Boiler Mixture

The low boiler mixture from stage d) was collected, admixed with 0.02 g of aqueous NaOH (25%) per gram of low boiler mixture and sent to a distillative separation ("low boiler distillation").

A packed column (DN 50 mm) with three sections of structured packing each of length 1 m and specific surface area 500 m$^2$/m$^3$ was used. The feed (approx. 4 kg/h) was above the second section. A top pressure of approx. 1.05 bar absolute was established. In the bottom, a temperature of 104° C. was established. The energy was supplied to the column by means of a natural circulation evaporator. The vapors obtained at the top were fed to a condenser; this precipitated the vapors obtained virtually completely at 30° C. Approx. 1500 g/h of the distillate obtained were discharged; approx. 1000 g/h were metered into the column as reflux at the uppermost packing section.

The resulting organic low boilers were collected and 1.5 kg/h were fed to a tray column (diameter DN 50 mm, 40 trays) ("TMA distillation").

The feed was at the 30th tray from the bottom. The column was operated at 5 bar gauge. In the bottom, the column was boiled by means of a natural circulation evaporator. A temperature of 130° C. (measured at the 5th tray of the column) was established. At the top of the column, the vapors were precipitated virtually completely in a condenser at 30° C. Approx. 140 g/h of the resulting condensate were discharged; 1.25 kg/h were recycled to the column as reflux to the uppermost tray. From the column bottom, approx. 1.35 kg/h (approx. 45% water, approx. 40% MeOH, approx. 15% IBOL (isobutanol), <100 ppm by weight of TMA, remainder organic components) were discharged.

The condensate discharged comprised >99% TMA (remainder predominantly methanol).

The residence time was approx. 11 minutes ($V_{holdup}$=30× 20 ml=0.6 l; $V_{feed}$=1.5 kg/h/0.8 kg/l=1.88 l/h, $V_{reflux}$=1.25 kg/h/0.8 kg/l=1.56 l/h).

The bottom product obtained from the TMA removal was collected and sent to a further distillative separation ("MeOH distillation"). A packed column (DN 50 mm) with three sequences of structured packing each of length 1 m and specific surface area 500 m²/m³ was used. The feed (approx. 1.3 kg/h) was above the second section. A top pressure of approx. 1.05 bar absolute was established. In the bottom, a temperature of 92° C. was established; the energy was supplied to the column by means of a natural circulation evaporator. The vapors obtained at the top were fed to a condenser, which precipitates the vapors obtained virtually completely at 30° C. Approx. 500 g/h of the resulting distillate (99.86% methanol, remainder predominantly methanol) were discharged; approx. 2000 g/h were metered into the column as reflux at the uppermost packing section.

The bottoms discharged in the bottom of the column were cooled to approx. 30° C. in a heat exchanger and collected in a phase separator. Subsequently, an organic phase (predominantly isobutanol, approx. 10% water, approx. 1% MeOH, remainder other organic components, 200 g/h with feed 1.3 kg/h) and an aqueous phase (approx. 90 or else more % water, approx. 5% isobutanol, approx. 2% methanol, remainder other organic components, 600 g/h with 1.3 kg/h of feed) were obtained.

EXAMPLE 2

Distillation of the Low Boiler Mixture in a Dividing Wall Column

The low boiler mixture from stage d) had the same composition as in example 1. The top product from stage d) was collected, admixed with 0.02 g of aqueous NaOH (25%) per gram of low boiler mixture and sent to a distillative separation ("low boiler distillation"). The "low boiler distillation" was effected analogously to the "low boiler distillation" in example 1.

The organic low boilers obtained from the "low boiler distillation" were worked up in a dividing wall column.

The resulting organic low boilers from the low boiler distillation were collected and fed at a regulated rate of 1 kg/h to a dividing wall column (tray column, diameter DN 80 mm, 60 trays, dividing wall from tray 16 to 45); the feed was at the 30th tray, or the 15th tray, on the feed side of the segment divided by the dividing wall. The column was operated at 2 bar gauge.

In the bottom, the column was boiled by means of a natural circulation evaporator. A temperature of 125° C. was established. At the top of the column, the vapors were condensed virtually completely in a condenser at 30° C. Approx. 100 g/h of the condensate obtained (>99% TMA, remainder predominantly methanol) were discharged; 4 kg/h were recycled as reflux to the column at the uppermost tray.

In the column, the liquid was collected completely above the dividing wall section. Approx. 1.75 kg of liquid were obtained. Approx. 500 g/h of these 1.75 kg were fed to the feed section; 1250 g/h were fed at a regulated rate to the product side. At the 30th tray or 15th tray of the dividing wall section, 350 g/h of methanol-rich liquid (>99.9% methanol, remainder predominantly water) were withdrawn from the column.

Approx. 550 g/h were discharged from the bottom of the column. The bottoms discharged in the bottom of the column were cooled to approx. 30° C. in a heat exchanger and collected in a phase separator. Subsequently, an organic phase (predominantly isobutanol, approx. 10% water, approx. 0.5% MeOH, remainder other organic components) and an aqueous phase (approx. 90 or else more % water; approx. 5% isobutanol, approx. 1% methanol, remainder other organic components) were obtained.

The aqueous phase was discharged. The organic phase was likewise discharged. The residence time in the dividing wall column was approx. 7 minutes ($V_{holdup}$=15×0.05 l=0.75 l; $V_{feed}$=1 kg/h/0.8 kg/l=1.25 l/h; $V_{reflux}$=4 kg/h/0.8 kg/l=5 l/h)

EXAMPLE 3

Comparative Example (Distillation of the Low Boiler Mixture)

The low boiler mixture from stage d) had the same composition as in example 1. The top product from stage d) was collected, mixed with 0.02 g/g of distillate of aqueous NaOH (25%) and fed to a distillative separation ("low boiler distillation").

The feed was 1.5 kg/h into, a tray column (diameter DN 50 mm, 40 trays). The feed was at the 30th tray from the bottom. The column was operated at 1 bar gauge. In the bottom, the column was boiled by means of a natural circulation evaporator (the evaporator may, however, also be another kind of evaporator, for example falling film evaporator). A temperature of 100° C. (measured at the 5th tray) was established. The bottom temperature was thus less than 110° C. At the top of the column, the vapors were condensed virtually completely in a condenser at 5° C. Approx. 150 g/h of the condensate obtained were discharged; 5 kg/h were recycled to the column as reflux to the uppermost tray. From the column bottoms, approx. 1.3 kg/h (approx. 45% water, approx. 39% MeOH, approx. 15% isobutanol, approx. 1% by weight of TMA, remainder other organic components) were discharged.

The residence time in the stripping section was approx. 4 minutes ($V_{holdup}$=30×0.02 l=0.6 l; $V_{feed}$=1.5 kg/h/0.8 kg/l=1.88 l/h; $V_{reflux}$=5 kg/h/0.8 kg/l=6.25 l/h)

The condensate discharged comprised approx. 95% TMA, approx. 1% water, approx. 4% MeOH.

The residue obtained from the TMA removal was collected and sent to a further distillative separation ("MeOH distillation"). A packed column (DN 50 mm) with three sequences of structured packing each of length 1 m and specific surface area 500 m²/m³ was used. The feed (approx. 1.3 kg/h) was above the second section. A top pressure of approx. 1.05 bar absolute was established. In the bottom, a temperature of 92° C. was established; the energy was supplied to the column by means of a natural circulation evaporator, but it is also possible to use another evaporator, for example falling film evaporator. The vapors obtained at the top were fed to a condenser; this precipitates the vapors obtained virtually completely at 30° C. Approx. 550 g/h of the distillate obtained (approx. 98% methanol, approx. 1% IBA, approx. 1% TMA) were discharged; approx. 2000 g/h were metered into the column as reflux at the uppermost packing section.

The comparison of example 1 with example 3 (comparative example) shows that the condensate of the second distillation stage ("TMA distillation") has a low methanol content only when the bottom temperature is more than 110° C. When the distillation is performed at lower temperatures, TMA which comprises even greater amounts of MeOH is obtained. Such methanolic TMA is less suitable for recycling into the aldol reaction than the TMA which was obtained by the process according to the invention.

EXAMPLE 4

Preparation of Crude Polymethylol with the Hydrogenation Process with TEA

Stage a) Aldol Reaction:

Approx. 750 g/h of isobutyraldehyde (approx. >99.5 GC area % of IBA) were reacted with approx. 700 g/h of formaldehyde (approx. 49% by weight of formaldehyde, 1.5% by weight of methanol, remainder water) and 30 g/h of triethylamine solution in a two-stage stirred tank cascade.

Stage b) Distillative Separation of the Reaction Mixture from Stage a):

Subsequently, the solution was freed of low boilers by distillation in a column. The column was equipped with 1.5 m of fabric packing (specific surface area 500 m$^2$/m$^3$) in the rectifying section and 4 m of sheet metal packing (250 m$^2$/m$^3$). The aldolization discharge was fed in above the sheet metal packing. At the top of the column, a condenser with cooling water (approx. 10° C.) and a downstream phase separator was used. At the top, the distillate was fed to the condenser in gaseous form. Approx. 227 g/h of liquid condensate were obtained. In the downstream phase separator, an aqueous phase of 55 g/h was removed and fed completely to the column. In addition, 80 g/h were fed from the phase separator to the first stirred tank of the stirred tank cascade of the aldol reaction. In order to maintain the regulated temperature in the column at 85° C., approx. 92 g/h of organic phase were additionally fed to the column. In the cold trap connected downstream of the condenser, approx. 1 g/h of liquid was obtained (approx. 90% by weight of IBA, approx. 1% by weight of TEA, remainder further organic components), which was likewise recycled.

The IBA removal was conducted at a top pressure of approx. 1 bar absolute. The evaporator used was a falling film evaporator. A bottom temperature in the bottom of the column of 103° C. was established. The reflux rate (or cooling water rate of the partial condenser) to the column was regulated by means of the temperature in the middle of the fabric packing. A temperature of 85° C. was established.

From the column bottom, approx. 100 kg/h of liquid were drawn off by means of a pump. These were fed to the falling film evaporator (consisting of an oil-heated stainless steel tube, length 2.5 m, internal diameter approx. 21 mm, wall thickness approx. 2 mm). From the bottom of the falling film evaporator, approx. 1.5 kg/h of product with a concentration of approx. 0.3% by weight of isobutyraldehyde were drawn off. The vapors and excess liquid were fed to the column bottom. The bottom product discharged comprised approx. 70% by weight of hydroxypivalaldehyde (HPA), approx. 1% by weight TEA, 1-2% TEA formate, approx. 1% by weight of hydroxypivalic acid neopentyl glycol ester (HPN), 0.6% by weight of IBA, remainder water.

Stage c) Hydrogenation of the Bottom Discharge from Stage b):

The resulting bottom product was subsequently subjected to a hydrogenation by means of a fixed bed.

The catalyst was activated as follows:

150 ml of a Cu/Al$_2$O$_3$ catalyst, as described in EP 44444, were activated in a tubular reactor at 190° C. by passing over a mixture of 5% by volume of hydrogen and 95% by volume of nitrogen (total volume 50 l (STP)/h) at ambient pressure for 24 hours.

The hydrogenation was performed as follows:

The starting solution used was the mixture described above as the hydrogenation feed. The feed was conducted in trickle mode at H$_2$ pressure 40 bar through the reactor heated to 120° C. The space velocity was 0.4 kg of HPA/(I$_{cat}$.*h). A portion of the hydrogenation discharge was added again to the feed (circulation mode). The ratio of circulation to feed was 10:1. The pH of samples of the reactor discharge at room temperature was measured at 8.

The composition of the aqueous polymethylol mixture from stage c) was:

NPG: 69% by weight
Methanol: 3.5% by weight
TEA: 1% by weight
Organic secondary compounds (HPS, n-butanol): <2% by weight
TEA formate: approx. 1% by weight
Water: approx. 23% by weight Stage d): Distillation of the Aqueous Polymethylol Mixture from Stage c):

The resulting discharge is collected and approx. 1.5 kg/h are fed to a distillative separation. A packed column (DN 50 mm) with three sequences of structured sheet metal packing each of length 1 m and specific surface area 500 m$^2$/m$^3$ was used. The feed was above the lowermost sequence. A top pressure of approx. 175 mbar absolute was established. In the bottom, a temperature of 160 to 165° C. was established; the energy was supplied to the column by means of a natural circulation evaporator. The vapors obtained at the top were fed to a condenser; this virtually completely precipitates the vapors obtained at 30° C. The vacuum was obtained by means of a simple commercial waterjet vacuum pump. Approx. 350 g/h of the resulting distillate ("low boiler mixture") were discharged; approx. 250 g/h were metered into the column as reflux at the uppermost packing section. The water used to obtain the vacuum was fed to a biological wastewater treatment.

The low boiler mixture from stage d) had the following composition:

10% by weight of methanol,
0.1% by weight of unconverted aldehyde,
0.5% by weight of alcohol (III, NPG),
1% by weight of tertiary amine,
1.5% by weight of TEA formate
0.2% by weight of methylolalkanal (II),
4% by weight of IBuOH
approx. 1% by weight of organic secondary compounds,
remainder water.

Distillation of the Low Boiler Mixture

The top product from stage d) was collected, admixed with 0.02 g of aqueous NaOH (25%) per gram of low boiler mixture and sent to a distillative separation ("low boiler distillation"). A packed column (DN 50 mm) with three sections of structured packing each of length 1 m and specific surface area 500 m$^2$/m$^3$ was used. The feed (approx. 4 kg/h) was above the second section. A top pressure of approx. 1.05 bar absolute was established. A temperature of approx. 103° C. was established in the bottom; the energy was supplied to the column by means of a natural circulation evaporator (however, it is also possible to use another evaporator, for example falling film evaporator). The vapors obtained at the top were fed to a condenser; this virtually completely precipitated the vapors obtained at 30° C. Approx. 1400 g/h of the distillate obtained were discharged; approx. 800 g/h were metered into the column as reflux at the uppermost packing section.

The top product from the first stage of the multistage low boiler distillation was collected, and sent to a distillative separation, the so-called "TEA distillation".

The feed of 1 kg/h was into a tray column (diameter DN 50 mm, 40 trays). The feed was to the 30th tray from the bottom. The column was operated at 2.5 bar gauge. In the bottom, the column was boiled by means of a natural circulation evaporator. A temperature of 125° C. was established (measured at the 5th tray of the column). At the top of the column, the vapors were precipitated virtually completely in a condenser at 30° C. Approx. 400 g/h of the resulting condensate (>29% TEA, approx. 3% water, 67% methanol) were discharged; 2.0 kg/h were recycled to the column as reflux to the uppermost tray. Approx. 0.6 kg/h were discharged from the column bottom (approx. 73% water, approx. 1% MeOH, approx. 24% isobutanol, <100 ppm by weight of TEA, remainder other organic components).

The residence time in the stripping section was approx. 10 minutes ($V_{holdup}$=30×0.02 l=0.6 l;
$V_{feed}$=1 kg/h/0.8 kg/l=1.25 l/h; $V_{reflux}$=2 kg/h/0.8 kg/l=2.5 l/h).

The bottom residue was cooled to approx. 20° C.; two phases formed, the organic phase (proportion by mass approx. 20%, approx. 78% isobutanol, approx. 18% water, 1% MeOH), and an aqueous phase (approx. 80%, approx. 84% water, approx. 15% isobutanol, approx. 1% MeOH).

The distillate obtained from the TEA removal was collected and sent to a further distillative separation ("MeOH distillation"). A packed column (DN 50 mm) with three sequences of structured packing each of length 1 m and specific surface area 500 m²/m³ was used. The feed (approx. 0.5 kg/h) was above the second section. A top pressure of approx. 1.05 bar absolute was established. In the bottom, a temperature of 75° C. was established; the energy was supplied to the column by means of a natural circulation evaporator; however, it is also possible to use another evaporator, for example falling film evaporator. The vapors obtained at the top were fed to a condenser; this precipitates the vapors obtained virtually completely at 30° C. Approx. 340 g/h of the resulting distillate (99.86% methanol, remainder predominantly water and TEA) were discharged; approx. 4.5 kg/h were metered into the column as reflux at the uppermost packing section.

The bottoms discharged in the bottom of the column were cooled to approx. 20° C. in a heat exchanger and collected (approx. 165 g/h, approx. 85% TEA, approx. 10% water, approx. 2% MeOH). After a prolonged residence time, two phases formed; the organic phase (approx. 150 g/h, 92% TEA) was collected and used in the aldol reaction.

The aqueous phase was discarded.

The invention claimed is:

1. A process for recovering components from a low boiler mixture which is obtained in distillation of hydrogenation effluents from preparation of polymethylols, wherein the low boiler mixture is prepared by
   a) condensing an alkanal in an aldol reaction with formaldehyde in the presence of a tertiary amine as a catalyst to give a reaction mixture comprising a methylolalkanal of the formula (II)

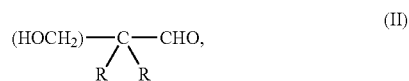

b) distillatively separating the reaction mixture into a bottom discharge comprising predominately the methylolalkanal of the formula (II),
   c) hydrogenating the bottom discharge, and
   d) distilling the hydrogenated bottom discharge and removing the low boiler mixture
and wherein the process for recovering components from the low boiler mixture comprises
   e) distilling the low boiler mixture comprising a tertiary amine, water, methanol, polymethylol of the formula (I)

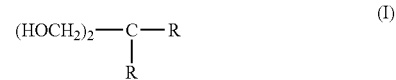

the methylolalkanal of the formula (II)

an alcohol of the formula (III)

and an alkanal with a methylene group in the α position to the carbonyl group,
and in which each R is independently a further methylol group or an alkyl group having 1 to 22 carbon atoms or an aryl or aralkyl group having 6 to 22 carbon atoms,
in a multistage distillation by separating the low boiler mixture in a first distillation stage into a higher-boiling, predominantly water-rich fraction and into a lower-boiling aqueous organic fraction comprising the tertiary amine, and
   f) separating the aqueous organic fraction from the first distillation stage in a second distillation stage into a predominantly amine-containing fraction and a further amine-depleted fraction,
wherein the tertiary amine is trimethylamine or triethylamine, and the bottom temperature in the second distillation stage is at least 110° C.

2. The process according to claim 1, wherein a base is added to the low boiler mixture before introduction into the first distillation stage.

3. The process according to claim 1, wherein the polymethylol of the formula (I) is neopentyl glycol, trimethylolpropane, pentaerythritol, trimethylolethane or trimethylolbutane.

4. The process according to claim 1, wherein the tertiary amine is trimethylamine.

5. The process according to claim 1, wherein the low boiler mixture comprises
   1 to 20% by weight of methanol,
   0.01 to 1% unconverted aldehyde,
   0.5 to 5% by weight of alcohol (III), 0.5 to 5% by weight of tertiary amine,
0.01 to 1% by weight of methylolalkanal (II),
0 to 5% by weight of organic secondary compounds, and the remainder water.

6. The process according to claim 1, wherein the bottom temperature in the second distillation stage is from 110 to 145° C.

7. The process according to claim 1, wherein the residence time in the second distillation stage is from 5 to 45 minutes.

8. The process according to claim 1, wherein the pressure in the second distillation stage is from 3 to 10 bar.

9. The process according to claim 1, wherein the predominantly amine-containing fraction is worked up and used as a catalyst for condensing the alkanal with formaldehyde.

10. The process according to claim 1, wherein the amine used is triethylamine and the predominantly amine-containing fraction from the second distillation stage is separated in a third distillation stage into a fraction which comprises predominantly tertiary amine and into a fraction which comprises predominantly water and/or methanol.

11. The process according to claim 1, wherein the amine used is trimethylamine and the aqueous organic fraction from the second distillation stage is separated into a methanolic phase and an aqueous organic fraction.

12. The process according to claim 10, wherein the second and the third distillation stages are performed together in one dividing wall column.

13. The process according to claim 10, wherein the triethylamine from the third distillation stage is used as a catalyst for condensing the alkanal with formaldehyde.

14. The process according to claim 11, wherein the trimethylamine from the second distillation stage is used as a catalyst for condensing the alkanal with formaldehyde.

15. The process according to claim 1, wherein the low boiler mixture is obtained by a multistage hydrogenation process involving, in stage a), condensing alkanals with formaldehyde in the presence of tertiary amines as a catalyst to give methylolalkanals of the founula (II), and then, in stage b), distillatively separating the reaction mixture obtained from stage a) into bottoms comprising predominantly compounds of the formula (II), and a topstream comprising low boilers, and, in stage c), hydrogenating the bottom effluent from stage b) and then, in a stage d), distilling the effluent from stage c), the low boiler mixture being removed from stage d).

* * * * *